United States Patent [19]
Roe et al.

[11] Patent Number: 5,500,220
[45] Date of Patent: Mar. 19, 1996

[54] BIOLOGICAL AND DUST CONTROL METHODS FOR BULK/GRANULAR SOLIDS

[75] Inventors: Donald C. Roe, Burlington, N.J.; Dwight P. Davis, Holland, Pa.; Kevin C. Manning, Richboro, Pa.; Edmund J. Bockowski, Furlong, Pa.

[73] Assignee: Betz Laboratories, Inc., Trevose, Pa.

[21] Appl. No.: 373,709

[22] Filed: Jan. 17, 1995

Related U.S. Application Data

[63] Continuation-in-part of Ser. No. 142,749, Oct. 25, 1993, abandoned, which is a continuation-in-part of Ser. No. 23,465, Feb. 25, 1993, Pat. No. 5,256,419, which is a continuation of Ser. No. 848,783, Mar. 10, 1992, abandoned, which is a continuation of Ser. No. 733,075, Jul. 17, 1991, abandoned, which is a continuation of Ser. No. 451,385, Dec. 15, 1989, abandoned.

[51] Int. Cl.$^6$ .................................................... A01N 25/24
[52] U.S. Cl. .......................... 424/410; 252/88; 252/106; 424/407; 424/408; 426/309
[58] Field of Search ..................................... 424/408, 407, 424/410; 252/88, 106; 426/309

[56] References Cited

U.S. PATENT DOCUMENTS

| | | | |
|---|---|---|---|
| 865,578 | 9/1907 | Ellis | 252/88 |
| 2,585,026 | 2/1952 | Moen et al. | 426/618 |
| 3,563,461 | 2/1971 | Cole, Jr. | 239/9 |
| 3,891,571 | 6/1975 | Lambou et al. | 252/354 |
| 4,136,050 | 1/1979 | Brehm | 252/88 |
| 4,400,220 | 8/1983 | Cole, Jr. | 134/18 |
| 4,428,984 | 1/1984 | Shimizu et al. | 252/88 |
| 4,479,820 | 10/1984 | Merk et al. | 71/67 |
| 4,551,261 | 11/1985 | Salihar | 252/88 |
| 4,569,989 | 2/1986 | Madison | 523/122 |
| 4,780,233 | 10/1988 | Roe | 252/88 |
| 4,795,590 | 1/1989 | Kent et al. | 252/307 |
| 4,795,764 | 1/1989 | Alm et al. | 521/107 |
| 4,847,067 | 7/1989 | Thomas | 424/639 |
| 4,857,209 | 8/1989 | Lyons et al. | 210/755 |
| 4,869,905 | 9/1989 | Sobek et al. | 424/406 |
| 4,946,311 | 8/1990 | Rosar et al. | 405/129 |
| 5,079,266 | 1/1992 | Bockowski et al. | 514/703 X |
| 5,183,944 | 1/1993 | Werle et al. | 568/465 |

FOREIGN PATENT DOCUMENTS 1106907  8/1984  U.S.S.R. .

*Primary Examiner*—John C. Bleutge
*Assistant Examiner*—Robert H. Harrison
*Attorney, Agent, or Firm*—Alexander D. Ricci; Steven D. Boyd

[57] ABSTRACT

A foam carrier for a dust control agent and a biological control agent is provided to control fugitive dust dissemination and biological activity in bulk/granular solids.

ized solid particles are
BIOLOGICAL AND DUST CONTROL METHODS FOR BULK/GRANULAR SOLIDS This application is a continuation-in-part of application Ser. No. 08/142,749 filed Oct. 25, 1993, now abandoned, which is a continuation-in-part of application Ser. No. 08/023,465, filed Feb. 25, 1993 now U.S. Pat. No. 5,256,419, which is a continuation of application Ser. No. 07/848,783, filed Mar. 10, 1992 now abandoned which is a continuation of application Ser. No. 07/733,075 filed on Jul. 17, 1991 now abandoned which is a continuation of application Ser. No. 07/451,385 filed on Dec. 15, 1989 now abandoned.

FIELD OF THE INVENTION

The present invention relates to methods of controlling dust and biological activity in bulk/granular solids.

BACKGROUND OF THE INVENTION

Dust dissemination poses safety, health and environmental problems in many commercial environments. For example, dust suppression is of particular concern in the coal mining industry where coal dust dissemination caused by wind or transit motion may lead to black lung disease if inhaled over lengthy periods of time. Ignition of small dust particles is also a concern. Similar concerns exist when other materials such as sulfur, phosphates, clays or other finely divided ores and minerals generate dust in handling operations, during mining, transportation, storage or use.

In addition to the mining industry, many other commercial activities also provide the potential for dust control problems. For instance, fertilizer dust has raised health concerns due to human and animal inhalation and also poses the problems of ignition or explosion. The cement industry also is concerned with fugitive dust dissemination during manufacture, transport and storage operations. The handling of grains such as corn and wheat gives rise to concerns with regard to dust dissemination.

Industrial sources of fugitive dust include open operations, leaks and spills, storage, disposal, transit and/or poor housekeeping where sundry finely divided solid particles are involved. In non-commercial settings, dust generation may pose health and safety problems, as with the fertilizer use, as well as housekeeping or aesthetic problems.

In combination with the concerns and problems involved with the manufacture, storage and handling of items inclined to the formation of fugitive dust, concerns related to biological organisms also exist with respect to these items. For example, the production of acidic leachate i.e., acid mine drainage, found in coal and coal refuse piles is related to biological activity in the piles. Surfactant based biocides have been known to reduce the population of bacteria responsible and thereby inhibit acid mine drainage. Dried sewage sludge which can be used as fertilizer or mixed with coal for use as a fuel exhibits both dust generation problems and odor caused by biological action. Similarly, grains such as corn and wheat and animal feed which exhibit well known problems with respect to dust generation could be beneficially treated with biological agents to control insect or rodent damage or spoilage.

Thus, in numerous areas where dry, bulk or granular solids are manufactured, stored and handled the combination Of dust generation and biological activity are of concern. Thomas, U.S. Pat. No. 4,847,067 discloses the treatment of grain or hay to control the moisture induced growth of mold. The treatment also provides dust control. The described treatment comprises an aqueous solution of one or more salts of propionic acid and a deliquescent material and preferably also a humectant. The aqueous treatment is sprayed onto the grain or hay.

The use of foams as dust control agents is known in the coal mining industry. For example, Cole U.S. Pat. No. 4,400,220 discloses the use of foam of a specific small bubble size to control dust in coal mining operations at the working face and at transfer points. Roe, U.S. Pat. No. 4,780,233 discloses a water insoluble elastomeric polymer and oil combination which may be applied in a foam carrier to inhibit dust dissemination. Ellis, U.S. Pat. No. 865,578 discloses a non-foam dust control agent for application to a road surface.

Other agricultural uses for foams are known such as for freeze control. For example, Cole, U.S. Pat. No. 3,563,461 discloses a system of applying foam to agricultural plants to inhibit freeze damage. Lambou et al., U.S. Pat. No. 3,891,571 discloses a foam containing whey solids for use as frost and freeze protection for plants. The foam of Lambou et al. can be used as a carrier for the surface application of agricultural chemicals such as herbicides, fungicides, etc.

SUMMARY OF THE INVENTION

The present invention is directed to an aqueous foam composition made up of a foam carrier for a dust control agent and a biological control agent. The combination of a biological control agent or agents and a dust control agent in an aqueous foam composition has been found to be a particularly effective control agent when dealing with bulk or granular solids. The dust control agent component of the present invention may include binders which function as dust control extenders to provide residual dust control. The foam may be composed of anionic, nonionic and/or cationic surfactants in aqueous solutions foamed in a conventional manner. As used herein, biological control agent includes water and/or oil based biocides, fungicides, or other pesticides.

The aqueous foam composition of the present invention has been found to be effective at applying a dust control and a biological control agent to bulk solids. The combination of the present invention may be applied during a transfer operation to control dust dissemination and biological activity such as odor, acid mine drainage and insect or pest damage. The use of a foam to apply the dust control agents and biological control agent provides maximum distribution of the minimal effective amount of active ingredients thereby minimizing costs as well as minimizing required treatment concentrations.

DETAILED DESCRIPTION OF THE PREFERRED EMBODIMENTS

The present invention provides a method of inhibiting dust generation and biological activity in bulk solid materials.

The method of the present invention may employ the application of a so-called "one drum treatment". The treatment is composed of foaming agents, dust control agents, and biological control agents. The bulk solids which are treated by the present invention include materials which tend to generate dust during manufacture, storage and handling and which also are desirably treated for control of biological activity. Examples include dried sludge, coal, animal feed, grains (including but not limited to corn and wheat) and absorbents such as cat litter. The dust and biological control agents are applied in a foam which can be intimately mixed with the material to be treated. The use of foam as a distribution medium allows effective application of the dust and biological control agents to bulk solids. The dust and biological control agents of the present invention are thereby applied to essentially the entire surface of the bulk solid as opposed to surface treatments such as spraying an already formed coal pile.

The foaming agents of the present invention may be composed of anionic, nonionic and/or cationic surfactants in aqueous solutions. The generation of the foam may be by any suitable means such as described in U.S. Pat. No. 4,400,220, Cole, the contents of which are hereby incorporated by reference. The use of such foams will provide dust control most effectively when applied during manufacturing and transfer operations. Exemplary surfactant foaming agents include alkyl aryl sulfonate, alkyl ether sulfate, alpha olefin sulfonate, alpha sulfo methyl ester, alkyl sulfosuccinate, alkanolamide, amine oxide, and betaines. For effective dust control during storage, water and/or oil based binders such as mineral or vegetable oils, elastomeric and water soluble polymers and lignosulfonate compositions may be desirable. Such binders or extenders provide more effective residual dust control.

The biological control agent(s) portion of the present invention may include water and/or oil based biocides, fungicides, and pesticides. The use of such biological control agents in combination with a dust control agent in a foam control agent package provides for effective distribution over the surface area of the bulk solid. Further, the application of a biological control agent in a foam system allows extremely efficient distribution of a relatively small amount of active material. For example, in typical prior art grain or animal feed treatment, large volumes of relatively concentrated gaseous fumigants are employed to distribute the fungicide throughout the mass of the grain. In the method of the present invention, because essentially all of the biological control agent ends up on the surface of the bulk solid, rather than escaping to the atmosphere, lower volumes and concentrations of biological treatment material may be employed.

Exemplary biological control agents include, but are not limited to, n-alkyl dimethyl benzyl ammonium chloride (and other quaternary ammonium biocides), dodecyl guanidine hydrochloride, acrolein (produced in situ from suitable precursors), methylene bisthiocyanate, bis-trichloromethyl sulfone, bromo-nitrostyrene, 2,2-dibromo-3-nitrilopropionamide, 5-chloro-2-methyl-4-isothiazolin-3-one (with 2-methyl-4-isothiazolin-3-one), 2-bromo-2-nitropropane-1, 3-diol, and decyl thioethyl amine, either alone or in combination.

The combination of a formulation containing methylene bisthiocyanate and bromo-nitrostyrene (Slimicide C-41) and an oil based binder (Betz DG-1259F) emulsified in water with a surfactant foaming agent (FlowPro® 1105) has been found to provide effective dust control as well as odor control when applied as a foam to a coal/sludge mixture. The commercial products (Slimicide C-41, Betz DG-1259F, and FlowPro 1105) are available from Betz Laboratories, Inc., Trevose, Pa. Such coal/sludge mixtures are kiln dried and employed as inexpensive fuels in cement plants or similar applications.

The application of a fungicide to grains (including but not limited to corn and wheat) in an aqueous foam composition would be effective at inhibiting the formation and dissemination of grain dust. Further, such a combination would provide effective control of insect damage. The highly efficient application of a fungicide such as acrolein generated in situ from a suitable precursor, see U.S. Pat. No. 4,851,583 Bockowski et al. in a foam would provide effective control at reduced active treatment levels.

The invention will now be further described with reference to a number of specific examples which are to be regarded solely as illustrative and not as restricting the scope of the invention.

EXAMPLES

Example 1

A sludge/coal mixture was dried in a kiln and treated with a foam control agent comprising:

0.12% C14–C16 alpha olefin sulfonate sodium salt 0.11% alkyl ether sulfate sodium salt 1.98% naphthonic process oil 0.001% polyisobutylene 0.05% Betz® Slimicide C-41

An untreated sludge/coal mixture exhibited a high level of dust generation and a strong odor and visible biological activity believed to be fungus or mold. The sludge/coal mixture treated with the aqueous foam composition exhibited a very low level of dust generation and no odor or visible evidence of biological activity. Betz® Slimicide C-41 is a broad spectrum biocide available from Betz Laboratories, Inc. of Trevose, Pa. The active biocidal agents are beta-bromo-beta nitro. Styrene (BNS) at 9.2% and methylene bis thiocyanate (MBT) at 4.9% (See U.S. Pat. No. 4,579,665, Davis et al. and U.S. Pat. No. 3,898,343, Swered et al.) All percentages are in weight percent.

The aqueous foam composition of the present invention would be similarly effective at inhibiting the formation of biologically induced acid waste, such as acidic leachate called acid mine drainage. When coal or coal refuse is stored in piles, aqueous drainage or leachate often is acidic. The acidic nature of the leachate is related to biological activity within the coal pile. Similar acidic waste can be found in other ore and mineral piles. Surfactant based biocides such as alkyl benzene sulfonates, and alkyl sulfates sprayed onto the coal piles have been shown to reduce the bacteria and inhibit the acid mine drainage. Dust dissemination is also a problem in such coal storage piles. The application of aqueous foam composition including dust control agent(s) and pesticidal control agent(s) and a binder during formation of such piles would provide effective dust control and inhibit biological activity throughout the pile, not just at the surface.

Grains (including but not limited to corn and wheat) and animal feed are often treated with mineral oil and/or water for dust control in a separate application from fumigation. Typically, post harvest pesticides such as methyl chloride, methyl bromide, aluminum phosphide, or certain organophosphates are employed for fumigation. The application of an aqueous foam composition which includes a dust control agent(s) and a post harvest pesticide (biological control agent(s)) during handling of the grain will provide more effective control than prior art treatments. The method of the present invention will effectively control grain dust as well as insect damage. In the treatment of grains and animal feed, it is desirable to limit the moisture content of the foam to avoid the undesirable addition of moisture of the material.

Example 2

Testing was conducted of the fumigant action of acrolein on stored-product insects and the feasibility of foaming acrolein (2-propenal, acryl-aldehyde). The testing involved (a) tests against 3 species of stored-product insects in space (without commodity), (b) tests of confined insects in the center of a mass of wheat and applying acrolein in the headspace above the wheat and (c) insects were exposed in random position in a grain mass and acrolein was placed in the mass evenly by mixing. Four species of insects were used: adult confused flour beetle, *Tribolium confusum* Jaquelin duVal; adult cigarette beetle, *Lasioderma serricorne*; larvae of black carpet beetles, *Attegenus unicolor*; and all life stages of rice weevil, *Sitophilus orvzae*.

Acrolein was compared to methyl bromide, which sees major farm use as a fumigant for soil and in post harvest storage. At $LD_{50}$, acrolein is from 4.2 times as toxic as methyl bromide against cigarette beetle adults; to 1.6 times as toxic as methyl bromide against confused flour beetle adults.

In penetration tests, acrolein was not as effective as methyl bromide. Thus, while acrolein exhibit good biological control activity, in application as a fumigant it is less effective, than prior art materials. However, applying acrolein in a foam control agent will spread the acrolein through the material being treated thereby obviating this "penetration deficiency".

Testing of the feasibility of foaming acrolein solutions and evaluation of the dust control efficacy of such foam control agents was undertaken. Three surfactants were selected for evaluation as foaming agents: Calsoft L-60 (sodium dodecylbenzene sulfonate) available from Pilot Chemical Co., Witcolate A (sodium lauryl sulfate) available from Witco Corp. and Tween 80 (polyoxyethylene (20) sorbitan monooleate) available from ICI American, Inc.

Testing was conducted by shaking solutions in covered glass jars with calibrations for measuring foam height. Foam height measurements were made immediately after shaking, and after 5 minutes to determine foam stability.

Dust control efficacy was determined by applying 0.5 grams of foam to 100 grams of wheat (about 0.5% moisture addition) and visually comparing relative dustiness of the treated wheat compared to control (no foam). A scale of 0–10 was used to designate relative dustiness, where 0=o dust and 10=maximum dustiness (control).

Tables I and II summarize the results of the testing which shows that acrolein can be foamed with a variety of surfactants and that foams containing acrolein are effective at reducing grain dust.

TABLE I

| Foaming Agent Surfactant | Surfactant Concentration (% Product) | Acrolein Concentration (% Product) | Foam Height in inches 0 minutes | Foam Height in inches 5 minutes |
| --- | --- | --- | --- | --- |
| Calsoft L-60 | 0.10 | — | 3.00 | — |
| Calsoft L-60 | 0.25 | — | 3.25 | — |
| Calsoft L-60 | 1.00 | — | 3.25 | — |
| Calsoft L-60 | 0.75 | 1.0 | 3.25 | 2.50 |
| Calsoft L-60 | 0.75 | 10.0 | 3.25 | 2.50 |
| Witcolate A | 0.25 | — | 1.75 | — |
| Witcolate A | 0.50 | — | 2.75 | — |
| Witcolate A | 0.75 | — | 3.00 | — |
| Witcolate A | 1.00 | — | 3.25 | — |
| Witcolate A | 2.25 | 1.0 | 3.25 | 1.75 |
| Witcolate A | 2.25 | 10.0 | 3.00 | 2.00 |
| Tween 80 | 1.00 | — | 1.00 | — |
| Tween 80 | 10.00 | — | 1.50 | — |
| Tween 80 | 10.00 | 1.0 | 1.50 | 1.50 |
| Tween 80 | 10.00 | 10.0 | 1.25 | 1.00 |

TABLE II

| Foaming Agent Surfactant | Surfactant Concentration (% Product) | Acrolein Concentration (% Product) | Foam Height in inches 0 minutes | Foam Height in inches 5 minutes |
| --- | --- | --- | --- | --- |
| Control | — | — | — | 10 |
| Calsoft L-60 | 0.75 | — | 0.5 | 1 |
| Calsoft L-60 | 0.75 | 1.0 | 0.5 | 2 |
| Calsoft L-60 | 0.75 | 10.0 | 0.5 | 1 |
| Witcolate A | 2.25 | — | 0.5 | 1 |
| Witcolate A | 2.25 | 1.0 | 0.5 | 1 |
| Witcolate A | 2.25 | 10.0 | 0.5 | 2 |
| Tween 80 | 10.00 | — | 0.5 | 2 |
| Tween 80 | 10.00 | 1.0 | 0.5 | 3 |
| Tween 80 | 10.00 | 10.0 | 0.5 | 2 |

While this invention has been described with respect to particular embodiments thereof, it is apparent that numerous other forms and modifications of this invention will be obvious to those skilled in the art. The selection of appropriate surfactants, foam extenders and biological control agents is primarily dependent upon the bulk solids to be treated and compatibility of the components. The appended claims and this invention generally should be construed to cover all such obvious forms and modifications which are within the true spirit and scope of the present invention.

What is claimed is:

1. A method of reducing the dissemination of fugitive dust particles into the atmosphere from grain and controlling biological activity in grain by applying an aqueous foam composition to said grain wherein said composition comprises more than about 0.2% surfactant as foaming agent and a biocidally effective amount of a biocidal control agent to control biological activity in said grain comprising acrolein.

2. The method of claim 1 wherein said composition includes a binder in an amount sufficient to provide residual dust control.

3. A method of reducing the dissemination of fugitive dust particles and applying a biocidal control agent to grain comprising applying a foamed aqueous surfactant solution, including acrolein as a biological control agent to control biological activity in said grain.

4. The method of claim 3 wherein said foamed aqueous surfactant solution includes a binder in an amount sufficient to provide residual dust control.

\* \* \* \* \*